(12) United States Patent
Clark et al.

(10) Patent No.: US 9,940,702 B1
(45) Date of Patent: *Apr. 10, 2018

(54) DELAYED PETROLEUM COKING VESSEL INSPECTION DEVICE AND METHOD

(71) Applicant: Custom Industrial Automation Inc., Hannon (CA)

(72) Inventors: Richard D. Clark, Hannon (CA); Daryl K. Rutt, Niagra on the Lake (CA); John David Stratton, Brampton (CA)

(73) Assignee: Custom Industrial Automation Inc. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/383,951

(22) Filed: Dec. 19, 2016

Related U.S. Application Data

(63) Continuation of application No. 14/826,109, filed on Aug. 13, 2015, now Pat. No. 9,524,542, which is a continuation-in-part of application No. 13/889,173, filed on May 7, 2013, now abandoned, which is a continuation of application No. 13/104,453, filed on May 10, 2011, now Pat. No. 8,436,898, which is a continuation of application No. 11/391,532, filed on Mar. 28, 2006, now Pat. No. 7,940,298.

(Continued)

(51) Int. Cl.
| | | |
|---|---|---|
| H04N 7/18 | (2006.01) |
| H04N 9/47 | (2006.01) |
| G01N 19/08 | (2006.01) |
| G01N 29/04 | (2006.01) |
| G06T 7/00 | (2017.01) |
| H04N 5/225 | (2006.01) |
| G06K 9/00 | (2006.01) |
| G01N 21/90 | (2006.01) |
| G01N 21/88 | (2006.01) |

(52) U.S. Cl.
CPC ....... *G06T 7/0004* (2013.01); *G01N 21/8851* (2013.01); *G01N 21/9072* (2013.01); *G06K 9/00718* (2013.01); *H04N 5/2251* (2013.01); *H04N 5/2256* (2013.01); *G01N 2021/8887* (2013.01); *G01N 2201/061* (2013.01); *G06T 2207/30164* (2013.01); *H04N 2005/2255* (2013.01)

(58) Field of Classification Search
CPC .......... G06T 7/0004; G06T 7/70; G06T 7/60; G06T 2207/30164; G01B 11/24; H04N 7/18; H04N 5/2251; H04N 5/265; H04N 2005/2255; H04N 5/2256; G01N 21/90; G01N 2201/061; G01N 21/8851; G01N 21/9072; G01N 2021/8887; G06K 9/00718

See application file for complete search history.

(56) References Cited

U.S. PATENT DOCUMENTS

| | | |
|---|---|---|
| 4,317,632 A | 3/1982 | Orphan et al. |
| 4,510,447 A | 4/1985 | Moyer |

(Continued)

*Primary Examiner* — Roberto Velez
*Assistant Examiner* — Tuan Le
(74) *Attorney, Agent, or Firm* — Jack D. Stone, Jr.; Scheef & Stone, L.L.P.

(57) ABSTRACT

This invention comprises a system and a method for inspecting the inside of delayed petroleum coking vessels to identify deformations, detect and determine the severity of other defects, and visually observe the inside of the inspected vessel.

15 Claims, 10 Drawing Sheets

Related U.S. Application Data

(60) Provisional application No. 60/671,961, filed on Apr. 15, 2005, provisional application No. 60/718,583, filed on Sep. 19, 2005.

(56) References Cited

U.S. PATENT DOCUMENTS

| | | | |
|---|---|---|---|
| 4,656,981 A | 4/1987 | Murata et al. | |
| 4,761,610 A | 8/1988 | Svegander et al. | |
| 4,763,070 A | 8/1988 | Huschelrath | |
| 4,989,823 A | 2/1991 | Chapman | |
| 5,115,136 A | 5/1992 | Tomasch | |
| 5,130,652 A | 7/1992 | Kawakami et al. | |
| 5,425,279 A | 6/1995 | Clark et al. | |
| 5,574,376 A * | 11/1996 | Topp | G01N 27/82 324/238 |
| 5,956,077 A * | 9/1999 | Qureshi | B25J 9/06 348/82 |
| 6,104,970 A * | 8/2000 | Schmidt, Jr. | B62D 55/32 701/2 |
| 6,400,146 B1 | 6/2002 | Roy | |
| 6,455,100 B1 | 9/2002 | Heimann et al. | |
| 6,822,443 B1 | 11/2004 | Dogaru | |
| 6,955,100 B1 * | 10/2005 | Barich | G01M 17/08 73/865.8 |
| 6,973,838 B2 | 12/2005 | Denis | |
| 7,940,298 B2 | 5/2011 | Clark et al. | |
| 8,436,898 B1 | 5/2013 | Clark et al. | |
| 9,524,542 B1 | 12/2016 | Clark et al. | |
| 2004/0016755 A1 * | 1/2004 | Gilbert | B65D 88/34 220/216 |
| 2004/0036859 A1 * | 2/2004 | Silverman | G01N 21/954 356/237.1 |
| 2004/0045329 A1 | 3/2004 | Farnham et al. | |
| 2004/0045379 A1 | 3/2004 | Silverman et al. | |
| 2005/0151661 A1 * | 7/2005 | Albarado | B23K 9/32 340/679 |
| 2005/0151841 A1 | 7/2005 | Nelson et al. | |
| 2009/0133515 A1 * | 5/2009 | Gershtein | B08B 9/049 73/865.8 |
| 2011/0106459 A1 * | 5/2011 | Christ, Jr. | G01N 21/892 702/42 |

* cited by examiner

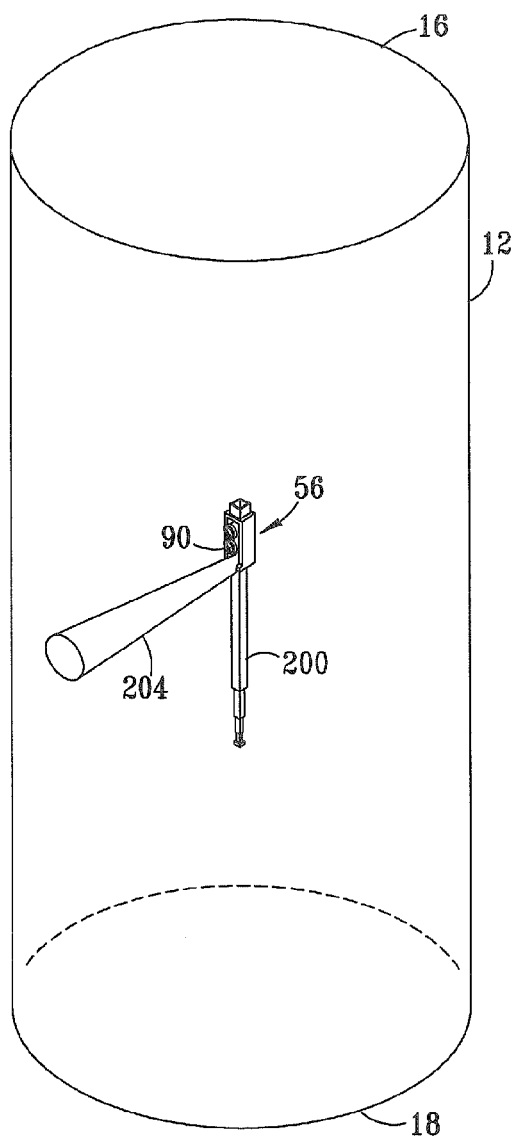
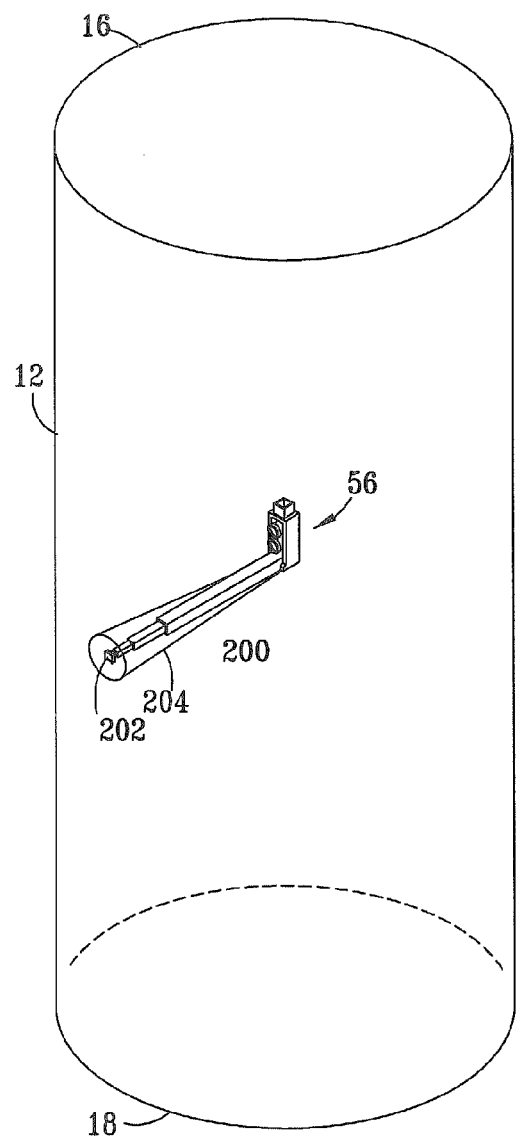

DELAYED PETROLEUM COKING VESSEL INSPECTION DEVICE AND METHOD

CROSS-REFERENCE TO RELATED CASES

This application is a continuation of application Ser. No. 14/826,109 filed Aug. 13, 2015, now U.S. Pat. No. 9,524,542 issued Dec. 20, 2016, which is a continuation-in-part of application Ser. No. 13/889,173 filed May 7, 2013, which is a continuation of U.S. Pat. No. 8,436,898, formerly Application Ser. No. 13/104,453 filed May 10, 2011, and issued on May 7, 2013, which is a continuation of U.S. Pat. No. 7,940,298, formerly Application Ser. No. 11/391,532 filed Mar. 28, 2006, and issued on May 10, 2011, which claims the benefit of U.S. Provisional Application No. 60/671,961, filed Apr. 15, 2005, and U.S. Provisional Application No. 60/718,583, filed Sep. 19, 2005, all of which applications are hereby incorporated herein by reference, in their entirety.

FIELD OF THE INVENTION

The present invention relates to systems for use to inspect the inside of delayed petroleum coking vessels to detect cracks and other defects.

BACKGROUND OF THE INVENTION

In many industrial systems, large vessels are used for various purposes. In many instances, these vessels contain materials which are at high temperature, high pressure or both and are vulnerable to failure. As a result, it is necessary that the inside of such vessels be inspected periodically. In the past, such inspections have been accomplished by simply emptying the vessel and physically inspecting the interior surfaces of the vessel. This permitted the detection of bulges, cracks, and pits and allowed for visual observation of the inside of the vessel. Some such vessels may be as large as twenty to thirty feet or more in diameter and fifty to seventy feet or more in height. One example of such vessels is petroleum coking vessels. These vessels are exposed to both thermal and mechanical stresses and are typically periodically inspected. The invention will be discussed primarily by reference to delayed petroleum coking vessels although the invention is equally useful with other large vessels.

Such vessels can be inspected by emptying the vessel and erecting scaffolding in the interior of the drum so that inspection personnel can make essentially manual inspections, including dimensional measurements to detect changes in the shape of the drum structure, visible defects and the like. Not only is this expensive and time consuming, inspection personnel are exposed to risks of released gases, falls and the like during the inspection process. Subsequently methods were developed, for instance as disclosed in U.S. Pat. No. 5,425,279 issued to R. D. Clark, et al. on Jun. 20, 1995 (the '279 Patent), which is hereby incorporated in its entirety by reference, for inspecting the interior of vessels using laser devices with reflective laser light being measured to detect and define bulges and other dimensional changes inside the vessel. This laser inspection technique was combined with the use of a video camera with both the laser system and the video camera being operable to provide recorded data by reference to the specific portions of the vessel tested. This data permitted the detection of bulges and the like and visual examination of the inside of the vessel. Unfortunately, since the vessels are not readily cleaned as they can be when inspection personnel enter the vessel, there may be coatings of material over the surfaces which prevent the detection of corrosion pits and the like in the interior surface of the vessel unless the pits or other irregularities have reached a size such that they can be detected by the laser system.

Coke drums typically have an outer shell of carbon steel or alloy steel ¾ to 1½ inches wall thickness and are internally clad with a layer of ferromagnetic stainless steel (410 stainless steel, for example) which can be up to 2.5 mm thick. The drums contain girth welds with weld caps up to two inches wide. The caps are normally low profile.

Before any inspection, the coke is cut from the internal surface of the drum using a high-pressure water cutter. This usually provides a relatively clean surface to enable the visual identification of crack indications.

Although very shallow craze cracking can exist in the liner, which does not in itself cause a problem, some cracks can grow to a significant depth and even penetrate into the substrate shell. While visual indications of surface cracking can be identified using the visual system, it is not currently possible to classify the cracking for depth in order to assess the severity of the cracking. Currently insulation has to be removed from the outside of the drum and ultrasonic testing is used to try and assess the crack depth. Apart from the cost involved in removing and replacing insulation, the ultrasonic testing is hampered by the cladding interface. Since these cracks can result in failures if severe, it would be highly desirable to determine the severity of the cracks, especially around weld areas, more easily and reliably and even more desirably in conjunction with the visual and laser testing.

SUMMARY OF THE INVENTION

A vessel inspection system for surveying the interior surface of a delayed petroleum coking vessel to identify defects in the vessel, the system including a device comprising: a frame; a support for supporting the frame for movement within said vessel along an axis; a rotary positioner adapted to position the frame rotationally with respect to the axis, and a vertical positioner for raising and lowering the frame; a recording system adapted to record the rotary position of the frame with respect to the vessel and the position of the frame along the axis within the vessel; an enclosure for electronics and optionally a source of pressurized gas connected to the enclosure to pressurize the enclosure to minimize incursion of combustible vapor into the enclosure; a video camera supported on the frame and operably connected to at least one of a monitor and a recording means for providing video monitoring of the interior surface of the vessel; a camera positioner supported on the frame and operable to position the video camera for viewing by the video camera, the camera positioner being operable to position the video camera about an axis perpendicular to the rotary positioner axis; a floodlight supported on the frame for illuminating the interior surface of the vessel for viewing by the video camera; a support on the vessel for clamping the support in a predetermined lateral and vertical position with respect to an axis of the vessel during operation of the system; an Alternating Current Field Measurement unit (ACFM), preferably mounted on a crawler positioned on an arm extension from at least one of the support and the frame for positioning the ACFM unit to test all or selected portions of the interior of the vessel; a crawler positioner for positioning the crawler and ACFM unit in selected locations; and a recorder for recording signals indicative of the ACFM unit position and the ACFM unit data from the selected locations.

A method for inspecting the interior surface of a delayed petroleum coking vessel, the method comprising: positioning a camera and a camera light in the vessel, the camera being positionable at a predetermined camera location relative to the longitudinal axis to record a video of the predetermined location; recording a plurality of videos at a plurality of predetermined camera locations and using the plurality of videos to provide a composite video of the interior surface of the vessel relative to the longitudinal axis; positioning an ACFM unit at a predetermined ACFM point on the interior surface of the vessel relative to the longitudinal axis and determining the presence and severity of cracks at the predetermined ACFM point; and determining the presence and severity of cracks at a plurality of predetermined ACFM locations in a selected ACFM tested portion of the interior wall and using the plurality of determinations to produce a planar development of the location of cracks and the severity of cracks in the ACFM selected portion of the interior wall.

BRIEF DESCRIPTION OF THE DRAWINGS

FIG. 6 is a schematic diagram of an inspection device in a vessel showing the positioning of a rotatable arm in its downward position inside a vessel;

FIG. 7 is a view of a similar inspection device with the arm in an extended position;

DESCRIPTION OF PREFERRED EMBODIMENTS

In the description of the Figures, the same numbers will be used throughout to refer to the same or similar components.

As noted previously, a system for photographing and inspecting the inside of a vessel for bulges and the like has been disclosed in U.S. Pat. No. 5,425,279 (the '279 Patent). The components of the present invention are suitably used in combination with the components of the '279 Patent, which are described as follows and in the '279 Patent.

Figure 1:
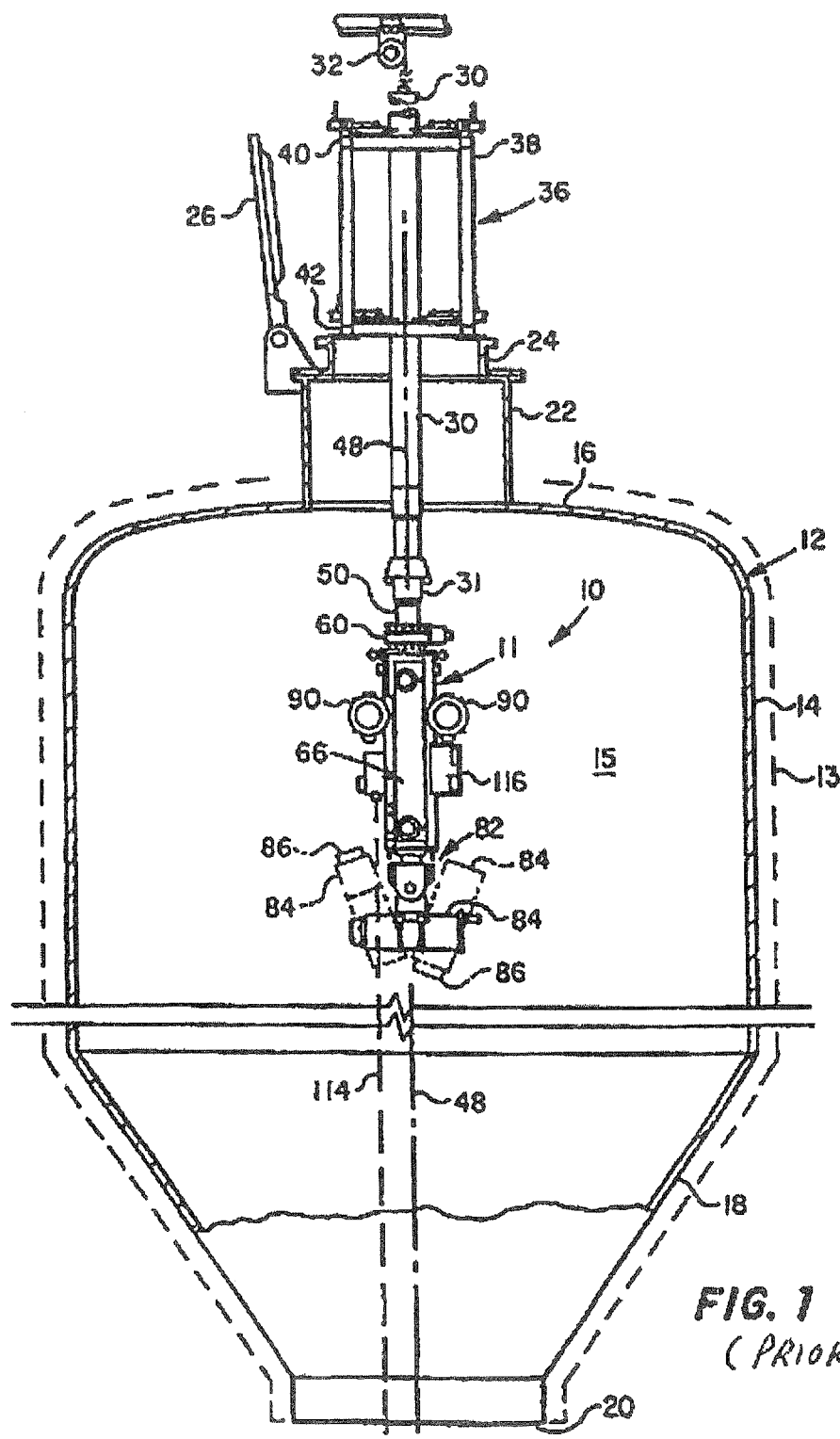
FIG. 1 is an elevation of a prior art vessel inspection system shown in place for inspecting the interior of a vessel, such as a delayed petroleum coking drum.

Referring to FIG. 1, there is illustrated a major part of a vessel inspection system generally designated by the numeral 10. The inspection system 10 includes a unique inspection device 11 shown disposed within the interior of a closable vessel 12 characterized as a delayed petroleum coking drum, although the vessel inspection system is also useful with other types of vessels. The coking drum 12 is a generally cylindrical vessel having a cylindrical sidewall 14, a head 16 and a frustoconical lower distal end portion 18 terminating in a bottom discharge opening 20 which may be closed by a suitable cover, not shown. The head 16 includes a cylindrical hatch delimited by a coaming 22, a flange 24 and a hinged cover 26 when in the open position. The vessel 12 is typically covered with an insulating blanket 13 over substantially its entire exterior surface.

FIG. 1 illustrates the inspection device 11 connected to an elongated stem 30 comprising a cylindrical pipe which extends into the interior of the vessel 12 through the manway or hatch coaming 22. The stem 30 is preferably suspended from a suitable motor operated hoist 32 disposed above the vessel 12 and operable to move the stem 30 from a raised position out of the interior 15 of the vessel to the position shown in FIG. 1 and to a further lowered position to allow the device 11 to inspect the entire interior surface of the vessel. In order to facilitate the use of the system 10 to make high resolution video recordings of the interior surface of the vessel 12 and to make precise measurements of distortion or dimensional changes in the general shape of the vessel, it is important to stabilize and clamp the stem 30 during operation of the inspection system 10.

Figure 2:
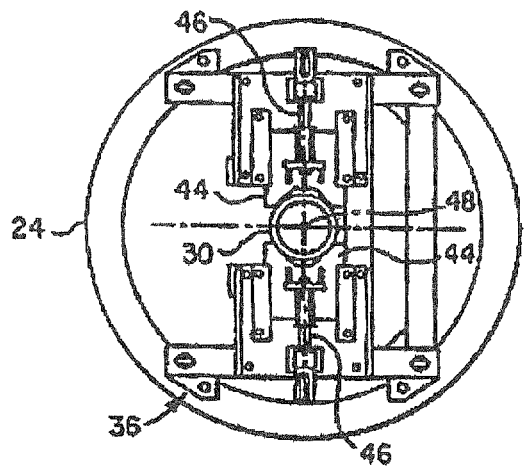
FIG. 2 is a plan view showing a prior art stem clamp unit mounted on a drum top flange.

Referring to FIG. 2, the stem clamp unit 36 includes a generally rectangular frame 38 having a chain type pipe clamp mounted on it, such as a clamp type manufactured by The Rigid Tool Company. The chain encloses the stem to releasably grip the stem 30 to centralize it along the central longitudinal axis 48 of the vessel 12 and to prevent lateral or vertical movement of the stem during operation of the inspection device 11. The stem 30 normally functions to carry a suitable coke drilling apparatus at its lower distal end 31 such as a high-pressure water jet type drill for cutting petroleum coke out of the interior 15 of the vessel 12 for discharge through the bottom opening 20.

Accordingly, the inspection device 11 may be conveniently mounted on the distal end 31 of the stem 30 in place of the drilling means, not shown. In this regard, a suitable coupling section 50 is provided for the inspection device 11 for releasably coupling the device to the lower end of the stem 30 when an inspection procedure is to be carried out.

Figure 3:
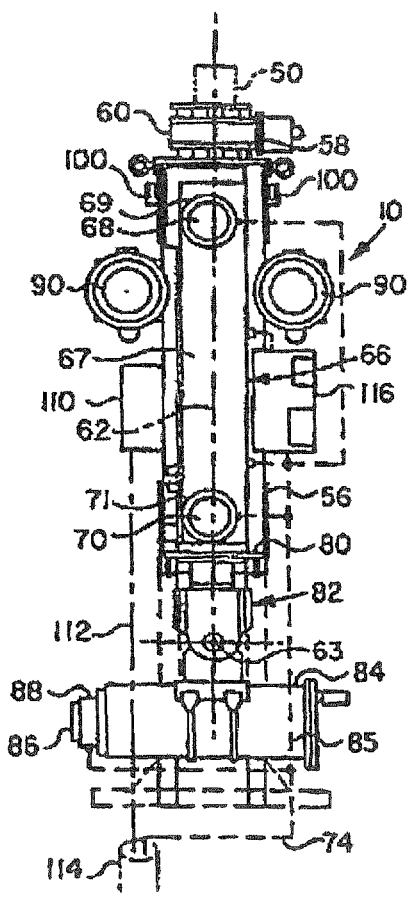
FIG. 3 is a front elevation of a prior art section device of the prior art system.
Figure 4:
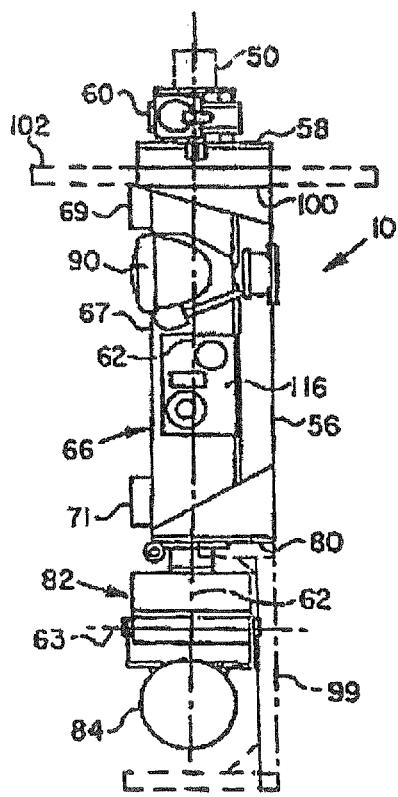
FIG. 4 is a side elevation of a prior art inspection device.

Referring now to FIGS. 3 and 4, the inspection device 11 is further characterized by an elongated frame 56, including an upper transverse flange part 58, which is suitably connected to a motor operated rotary positioning mechanism 60.

The rotary positioner 60 is also adapted to be connected to the coupling part 50 and is operable upon command by remote control, to rotate the inspection device 11, including the frame 56, with respect to the coupling 50 about a central axis 62 which, in operation of the device 11, coincides with an axis 48 of vessel 10. The frame 56 also supports an inspection or survey apparatus, generally designated by the numeral 66, for measuring the distance between an axis 62 and an interior surface of the vessel.

The frame 56 includes a lower transverse flange 80 on which is mounted a motor operated positioning mechanism, generally designated by the numeral 82, for supporting and positioning a camera 84 having a viewing lens 86 protected by an air curtain shroud 88. The camera 84 is suitably mounted on the positioning mechanism 82 for positioning the camera lens 86. Accordingly, the camera 84 may be tilted about an axis 63 to view the entire interior surface of the vessel 12, for example. The camera 84 is enclosed in an explosion-proof housing 85 and the air curtain shroud 88 is also in communication with a conduit 74 to receive lens washing gas therefrom. The camera 84 may be of a type operable to have a minimum resolution of 300 equivalent standard television lines and may be of a type commercially available such as a Model SSC-C370 12vDc manufactured by Sony Corporation of Park Ridge, N.J. The lens 86 may also be of a type commercially available such as a Model C-31002 manufactured by Cosmicar and having a "zoom" or magnification ratio of about 12 to 1 with remote control of zoom and focus.

As shown in FIGS. 3 and 4, the device 11 also includes a projecting floodlight 90 which is operable to illuminate the interior surface of the vessel 12 for suitable viewing by the camera 84. The floodlight 90 may be of a type available from Cooper Industries, Inc., Houston, Tex., under the trademark Crouse Hinds as Model RCDE-6.

As shown in FIGS. 1 and 3, electrical control signals to and from the positioner 60, the apparatus 66, the positioning unit 82, the camera 84 and the floodlights 90 may be carried by suitable conductors, not shown, through a suitable junction enclosure 110 mounted on the frame 56 and then through a suitable bundled conductor 112 which may be disposed in a sleeve 114 together with the conduit 74. The multi-conductor cable and sleeve assembly 114 may extend from the interior 15 of the vessel 12, for example, through the bottom opening 20 to a suitable control console to be described in further detail herein.

As shown in FIG. 3, instrument air or purge gas may be conducted to a suitable control unit 116 mounted on the frame 56 and operable to monitor the flow of purge gas to and from the enclosure 67 of the apparatus 66. The control unit 116 may also be of a type commercially available such as a Model 1101A, manufactured by BEBCO. Basically, the control unit 116 monitors the pressure within the interior of the enclosure 67 and operates a suitable alarm if the pressure decreases below a predetermined value indicating a possible leak of purge gas of unacceptable proportion from the enclosure 67.

Figure 5:
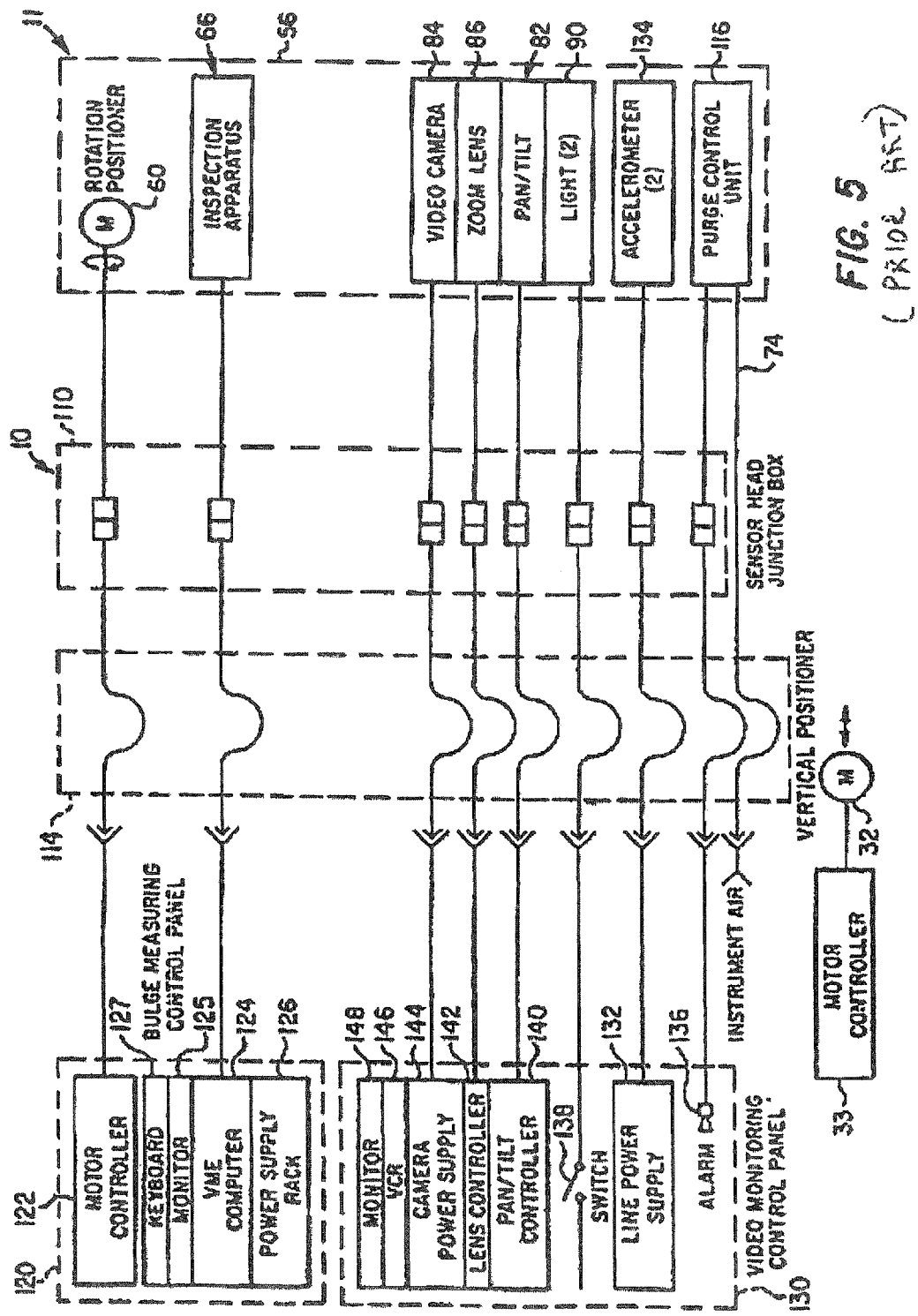
FIG. 5 is a schematic diagram of major elements of a prior art system.

Referring now to FIG. 5, there is illustrated a block diagram of the major components of the system 10 including those components disposed on the frame 56. As illustrated in FIG. 5, the vertical positioning hoist 32 is operable by a suitable controller 33 for positioning the stem 30 and the device 11. FIG. 5 also shows the control console may be divided into two separate control panels, one for controlling the operation of the system 10 to make dimensional measurements or so-called bulge measurements of the section 14 of the vessel 12 and a separate control panel for operating the video camera 84. As illustrated in FIG. 5, a control panel 120 may be provided to include a controller 122 for operating the rotation motor of positioner 60 and a digital computer or central processing unit 124 for controlling the operation of the inspection or survey apparatus 66 and for receiving data from the apparatus 66 to provide data and a suitable visual display of the dimensional changes in the surface of the section 14. The control panel 120 also includes a rack mounted power supply unit 126 for supplying power to the apparatus 66. The power supply unit 126 is operable to supply electrical power to the processing unit 124 also.

The processing unit 124 may be of a type operable to run on MS DOS based software, such as a so-called IBM type compatible computer. The processing unit 124 is equipped with a suitable visual monitor 125 and keyboard 127 and is adapted to be programmed to calculate, store and coordinate data received from the apparatus 66 and display related images on the monitor 125.

Referring further to FIG. 5, the control console also includes a video monitoring control panel 130. A suitable audio and/or visual alarm 136 is also provided on the panel 130 to indicate when a possible leak is occurring in the enclosure 67 to the apparatus 66. As illustrated, the panel 130 includes a suitable switch 138 for controlling the floodlights 90, a control unit 140 for the tilt positioning unit 82 and a controller 142 for operating the zoom lens 86.

The camera 84 is operably connected to a suitable power supply 144, a video recorder 146 and a suitable video monitor 148, all at the panel 130.

An operation to inspect the interior of a vessel such as the drum 12 is preceded by removal of all material from the interior 15 of the vessel, opening the hatch cover 26 and providing access to the bottom opening 20. The inspection device 11 can be inserted into the vessel through either the top flange 24 or the bottom flange 20 depending upon requirements unique to each site. In the embodiment shown, the inspection device is inserted through the top. Preferably, the temperature within the interior 15 is reduced to about 100° F. and when the inspection device is inserted through the bottom, the stem 30 is typically lowered to a point so that the lower distal end 31 is below the bottom flange 20. The inspection device 11 is then connected to the stem which is then positioned vertically in the vessel such that the starting elevation of the scan is coincident with the bottom tangent line of the vessel. The control cable assembly 114 leading to the control console which includes the panels 120 and 130 is connected to the device 11 and raised accordingly through the vessel 12. The series of operations is hereinafter referred to as "Bottom Entry Method". A similar method is necessary to insert the inspection device 11 through the top flange 24, hereinafter referred to as "Top 5 Entry Method". At this time the stem 30 may, if not previously adapted, be provided with a suitable linear measurement scale or tape measure, for example, suitably connected to its exterior surface for reference of the vertical position of the device 11 once it is lowered into the interior 15. Alternatively, the hoist 32 may be provided with a suitable readout device to indicate linear movement of the stem 30. Once the control cable 114 is suitably connected to the device 11 and to the control console, the inspection device 11 is positioned at the starting point of the inspection and the chain clamp then secures the stem 30 prior to initiating the scanning sequence at a particular elevation. The position of the device 11 with respect to the flange 24 is noted for each vertical change in position of the device within the interior of the vessel 12.

When the device 11 has been positioned at the starting point of the inspection, the clamp unit 36 is installed on the flange with the clamping jaws 44 retracted so that they may be positioned around the stem 30. When the clamp unit 36 has been suitably secured to the vessel 12 and the device 11 positioned in an initial position for inspecting the interior of the vessel, the chain on the pipe clamp is secured to the stem holding it in a centralized position aligned with axis 48.

Once the device 11 has been centralized and is ready for operation, an inert pressure gas or so-called instrument air is supplied through the conduit 74 to pressurize the enclosure 67 and to begin washing the lenses 68, 70 and 86. Proper pressurization of the enclosure 67 is verified through the control unit 116 by a lack of an alarm signal from the alarm 136. Verification of the operability of the positioners 60 and 82 together with the operability of the camera 84 is verified.

At this point the floodlights 90 may be illuminated and an overall view of the interior surface of the vessel may be initiated by operation of the camera 84 using the camera positioner 82 and the lens controller 142 to cause the lens 86 to magnify an area of interest on the monitor 148.

According to the present invention, an Alternating Current Field Measurement (ACFM) unit is used to measure the severity of various defects in all or a portion of the inside surface of a vessel. Many such vessels are used in industrial applications. Typically such vessels in the past have been inspected by manual inspection by the use of scaffolding and the like or by the use of techniques such as disclosed in the '279 Patent as disclosed above. Particularly, when a plurality of inspections have been made over time, it is beneficial to compare the inspection results to each other. This enables the operator of the vessel to determine whether there have been changes in its dimensions over time. The measurements by the laser unit are coordinated by the use of a positioning system which receives the data and coordinates it with the position of the laser in the vessel. As indicated earlier, such techniques are disclosed in the '279 Patent.

This laser system is used in conjunction with a video camera and a light source so that the light source and video camera can prepare pictures of the inside of the vessel. These pictures are also coordinated so that pictures are available for the entire internal surface of the vessel or any desired portion thereof. The coordination of the images is done by methods well known to those skilled in the art.

By the use of this remotely positioned system, which includes the laser system, the video camera and light system mounted on a frame supported inside the vessel, it is not necessary to clean the inside of the vessel prior to inspection, although the coke will have previously been removed using a high pressure water jet. While certain features such as welds and the like can be discerned, the inside of the vessel is not clean to the extent that small corrosion pits and the like can be detected unless they reach a size such that they can be detected by the laser system or become visible. Even when visible, the use of the light and the laser does not provide information about the depth of any crack, especially if the crack is positioned at least partially under an interior cladding.

Accordingly, it would be highly desirable to determine the presence and severity of these defects before serious corrosion or other types of pitting can occur. Since these types of pitting are more common near weld areas than over the entire vessel inside surface, in many instances it may be desirable to inspect only the weld areas, although other areas can also be tested if desired.

Alternating Current Field Measurement (ACFM) is added to the current inspection tool to provide crack detection and sizing capability. The main use for the ACFM system is to distinguish between shallow surface cracking (<2 mm (0.08″) deep) and more serious cracking which may require further examination and evaluation.

ACFM is a proven tool for accurately sizing fatigue defects for length and depth in ferrous structures and is an electromagnetic technique for detecting and sizing flaws breaking the inspection surface of both ferrous and non-ferrous metals and alloys. It operates using a probe which induces a locally uniform alternating current (AC) field into the test surface. This field flows in a thin skin in the surface of the material and is disturbed by the presence of surface breaking defects. These changes are detected by two types of sensors mounted in the probe which measure the magnetic field strength in two orthogonal directions. One sensor, termed the Bx sensor, measures the reduction in flux density around the center of the crack which is predominantly caused by the defect's depth. The other sensor, termed the Bz sensor, produces a response due to the curvature of the currents flowing around the ends of the defect. This sensor indicates the position of the defect ends and hence the surface length can be determined. The ACFM equipment is computer controlled and all inspection data is recorded for further investigation or for audit purposes. This system is capable of inspecting through non-conductive coatings of up to 5 mm thick. There is a reduction in sensitivity to shallow defect as the coating thickness increases and it is usual to determine a compromise between maximum coating thickness and minimum defect size.

According to the present invention an ACFM unit is used in combination with the camera and the laser to determine whether crack defects exist in the vessel and determine the severity of such defects if present. While the ACFM unit could be used alone with a suitable positioning and recording system, it is conveniently used in combination with the camera and laser positioning systems to provide a complete vessel inspection. The camera enables the positioning of the ACFM unit at welds or other areas which are visibly of interest for the ACFM testing. The ACFM unit can be passed along welds and other areas which are more highly vulnerable to stress cracking, corrosion, pitting and the like. The measured information is then passed to a recorder which coordinates it by reference to the position of the ACFM unit in the vessel. The ACFM unit positioned in the vessel could also be coordinated by use of the camera positioning since it is desirable to use the light used in combination with the camera to light and photograph sections of the inside of the vessel during ACFM testing. The ACFM unit is desirably situated on an extendable arm which permits it to be extended into contact with the inside of the vessel.

In FIG. 6 a schematic diagram is shown of such a system. A vessel 12 having a top 16 and a bottom 18 is shown. The system includes a camera (not shown) and floodlights 90 which are supported from frame 56. An extendable arm 200, including on an end portion an ACFM unit 202, is shown in a downward position as mounted on frame 56 for entry into vessel 12. The frame is not shown in detail but can be similar to the frame disclosed above. The arm is mounted on the frame in a downwardly extending direction. The arm is rotatable and includes an adjustably extendable end portion to support the ACFM unit on a selected portion of the interior wall at a pressure sufficient to allow magnetic rollers (not shown) positioned on the ACFM unit to engage the wall and retain the ACFM unit in close moveable contact with the wall. While magnetic rollers are effective to engage the ACFM unit with the inside wall at a desired spacing and to move the ACFM unit along the surface, these functions could also be performed by the arm.

The ACFM sensor head will be composed of an array of individual sensors incorporated into an integral package. The size and spacing of the sensors are configured depending on the target defect size and other operating factors. A suitable sensor configuration will detect defects of 0.25" (0.4 mm) long×0.1" (2.54 mm) deep. Different sensitivities could be used if desired. If it is desired that scan coverage is of prime importance, individual sensor spacing would be set to the estimated maximum allowable for the detection of the minimum size defect. A typical sensitivity is listed below:

Number of channels: 32 (16 Bx and 16 Bz sensors)
Number of fields: 1
Sensor diameter: 5 mm (0.2")
Sensor pitch: 7.2 mm (0.28")

A suitable ACFM unit is available from TSC Inspection Systems as model Amigo ACFM Vrack Microgauge. A variety of ACFM units may be used dependent upon the users and objectives.

Using twin fields provide information on transverse cracks and aids in the identification and categorization of some spurious signals. Alternatively a single field could be used which would confine crack identification and sizing to the circumferential direction, however it would allow more sensors to be used for circumferential sensing leading to a smaller spacing between sensors and/or a larger coverage. Such variations are well known to the art to achieve the specific objectives of the user.

It is necessary to house some low power electronics in the sensor assembly itself to select and amplify the individual sensor readings before transmission down the probe umbilical. The power supply to the ACFM probe as shown is a 9 volt dual rail unregulated supply. The maximum voltage that could be produced is 24 volts with a worst case short circuit condition leading to a maximum current draw of 1.5 A.

It is desirable to make the ACFM probe assembly as light as possible and desirably the weight of the probe is less than one kilogram (2.2 lbs) if conventional probe construction materials can be used for the outer casing. These materials are normally strong, machinable plastics.

Wheels or rollers may be fitted to the probe body to allow easy movement of the probe over the surface. These wheels may be magnetic and will desirably hold the ACFM unit in close contact with the interior wall. Forced air cooling or other gases may be used for cooling or to limit the pressure of combustible gases in the ACFM unit.

In FIG. 7 a similar vessel is shown with extendable arm 200 in a raised position and with the ACFM unit 202 extended into engagement with an inside surface 206 of vessel 12. A light zone 204 is shown on the inside wall of vessel 10 in conjunction with the location of ACFM unit 202. While desirably the light source is supplied by the same light source which supplies light for the camera and coordination of the camera and the ACFM unit may be used to also identify the location of the measurements taken by the ACFM unit, it is not necessary that this be done. In other words, the ACFM unit could also be equipped with its' own positioning and monitoring system which could provide the data and location coordinates to a recording system.

Figure 8:
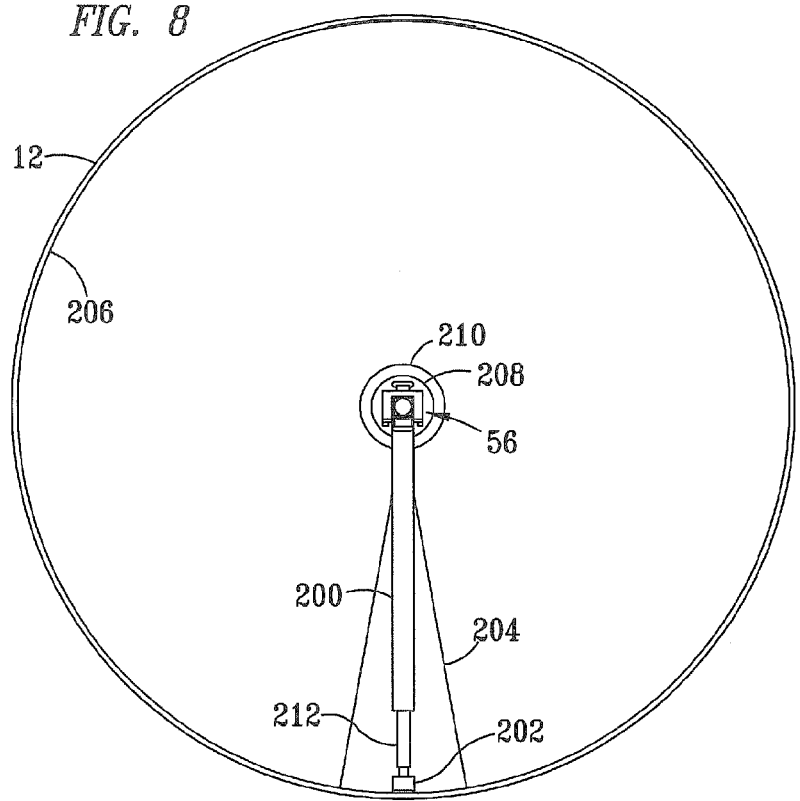
FIG. 8 is a cross-sectional view of an inspection device in an inspection device in a vessel with the arm in an extended position.

In FIG. 8 the system is shown from a top view in more detail. Particularly, circles 208 and 210 are shown representing a typical coke drum opening at the top with circle 208 representing the smallest coke drum top opening known to Applicants. The inside of vessel 12 is shown as surface 206 with a frame 56 supporting extendable arm 200 to support ACFM unit 202 in contact with inside wall 206 of vessel 12. Extendable arm 200 includes an extensible portion 212 as shown. As known to those skilled in the art, data is readily collected and coordinated with respect to the section of the inside surface of vessel 12 tested. As previously indicated, it is anticipated that many users may selectively test only the inside of the welds on the inside of the vessel. The welds can be readily located visually by the camera monitor.

Figure 9:
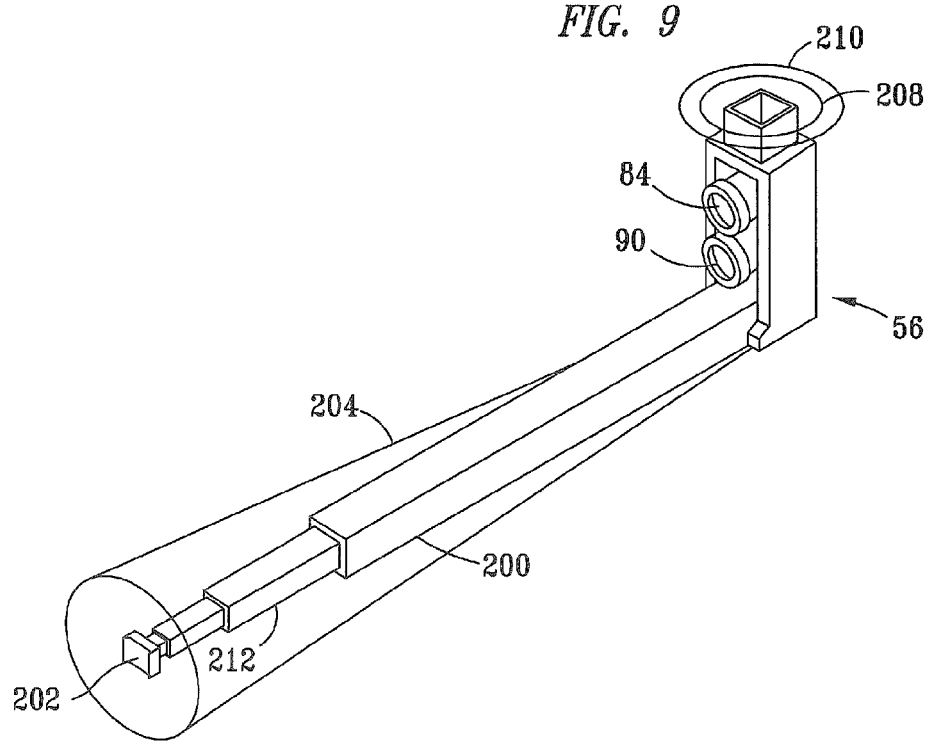
FIG. 9 is a schematic diagram of the arm supported from a frame of an inspection device which also includes a camera and light source.

In FIG. 9 a larger schematic diagram of an embodiment of the present invention is shown. In this embodiment ACFM unit 202 is shown in a light cone 204 as it engages the inside 206 of the vessel. Extendable arm 200, including extensible portion 212, is positioned from a frame which also includes a camera 84 and a light source 90.

While the ACFM unit has been shown as a wheeled unit which is maintained in position by an extendable arm, it should be noted that the wheels may be magnetized or non-magnetic. The requirement is for a suitably close engagement with the inside wall of the vessel. The wheels may be driven if desired or the rotational movement may be supplied by the extendable arm.

Figure 10:
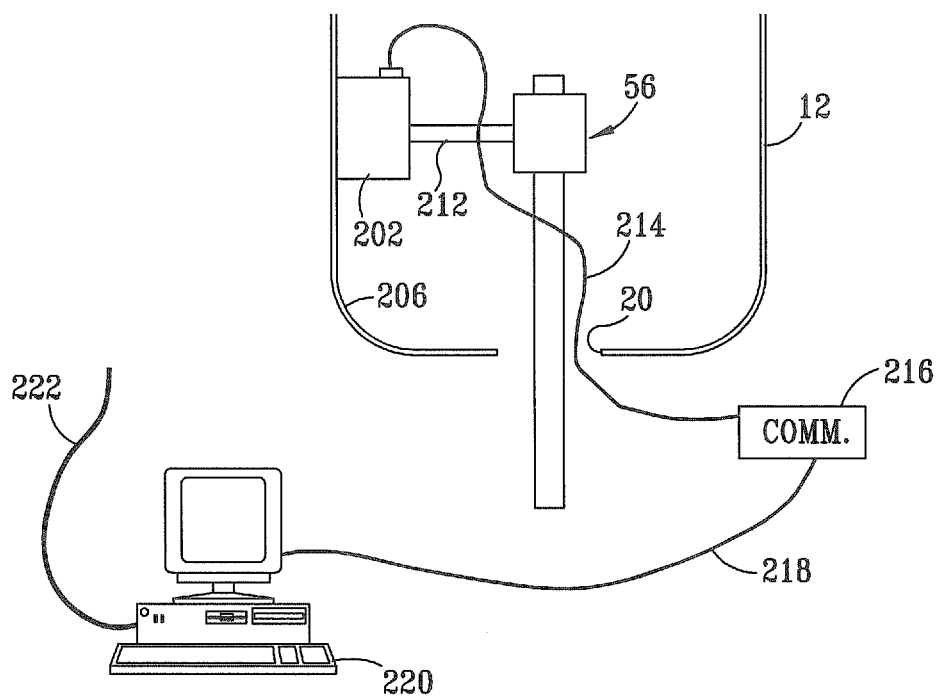
FIG. 10 is a schematic diagram of the system for detecting and determining the severity of cracks.

The system is shown schematically in FIG. 10. ACFM unit 202 is positioned on inside wall 206 of vessel 12 by an extendable arm 212. Positioning data and test data re passed via a line 214 to a communication device 216 and then via a line 218 to a PC controller 220 powered via a line 222 by a 110 volt power supply. The ACFM unit is supported on a frame 56.

Such a frame also typically includes a laser system and a camera system for making the measurements described by the '279 Patent.

Figure 11:
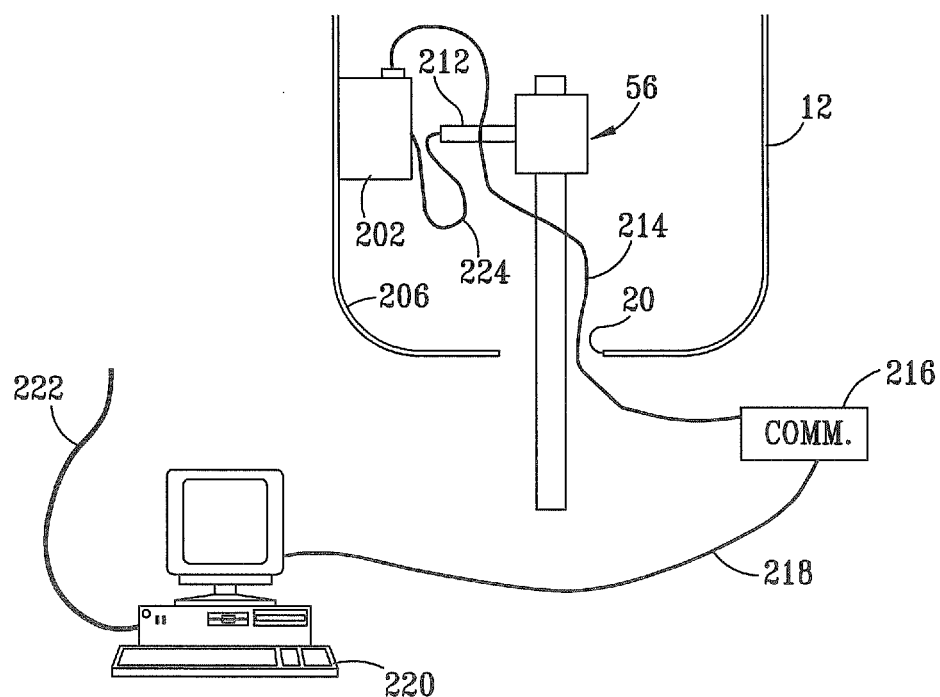
FIG. 11 is a schematic diagram of the system of FIG. 10 with the ACFM unit connected to the arm by a tether.

In FIG. 11 an embodiment similar to FIG. 10 is shown. In this embodiment, however, the ACFM unit is supported on magnetic wheels at a selected distance from the inner surface of the vessel. The ACFM unit moves by rotational power to the wheels at a selected pace. The rotatable arm trails the ACFM unit and supplies power, air and receives data and the like as necessary to achieve the desired testing via a tether 224. The ACFM unit is free to move independently of the extendable arm to the extent it does not exceed the length of the tether. The ACFM unit is retrievable by the extendable arm by simply withdrawing the tether and drawing the ACFM unit back into engagement with the extendable arm.

A variety of mechanical arrangements can be used to achieve these objectives. Particularly the supply of air and power to the ACFM unit are supplied in substantially the same way as supplied to the laser and the camera in the '279 Patent. Similarly, the data transmission from the laser survey system, the camera system and the ACFM unit may be transmitted in the same way to a PC station or other computer station, where the data is analyzed and the profiles of the inside wall of the vessel and the like are prepared are accomplished in a similar fashion as known to the art.

Similarly ACFM units are well known as discussed in the various patents submitted in the Information Disclosure Statement submitted herewith.

By the method of the present invention, not only are bulges and other large irregularities in the inner surface detected by the laser unit and not only are surface observations possible but by the combination the location of the ACFM unit can be controlled using the same frame or a similar frame as that used in the '279 Patent to analyze surface cracks which previously could only be observed at the surface. This permits the owner and operator of a large vessel, which has been discussed herein as a coke drum but which could be any type of large vessel, to determine not only whether the vessel has bulged or otherwise deformed but also whether there are dangerous cracks in the areas tested by the ACFM unit. This is a substantial advance in the testing of the vessel to ensure safe operation and avoid catastrophic vessel ruptures and failures.

Upon completion of a survey of the vessel 12, the clamp assembly 36 is removed from the flange 24 and the stem 30 is raised to remove the device 11 from the interior 15. The stem 30 is then returned to normal operation and the inspection system 10 is removed from the vicinity of the vessel 12, including the aforementioned control console and related components.

As discussed previously, the ACFM unit and the extendable arm are desirably mounted on the lower portion of the frame at a distance below the lower portion of the frame sufficient to avoid interference with the motion of the camera in panning actions and the like. This permits the extensible arm to be extended downwardly carrying the ACFM unit into the interior of the vessel. Upon reaching a selected level, the extensible arm is rotatable to a substantially perpendicular position or to other positions as may be desired. The ACFM unit is then positioned against the wall of the vessel and moves either by its own motion (self-propelled) with magnetic wheels and a suitable driving motor or by motion of the extensible arm around the vessel at a selected rate. The smaller the defects selected for detection, the slower the scanning rate must be and the more sensitive the testing apparatus contained in the ACFM unit must be. These criteria are readily selected by those skilled in the art for the type and size of defect which is to be determined. While it appears in FIGS. 10 and 11 that the cables are loose in vessel 12, such is not the case. Typically the contact cables and the like are contained in frame 56 so that the cables are relatively compact and controlled.

FIGS. 12-19 depict details of a vessel inspection system according to an alternate embodiment of the present invention. Since the vessel inspection system contains many components that are identical to those of the previous embodiment, these components are referred to by the same reference numerals and will not be described in any further detail.

Figure 12:
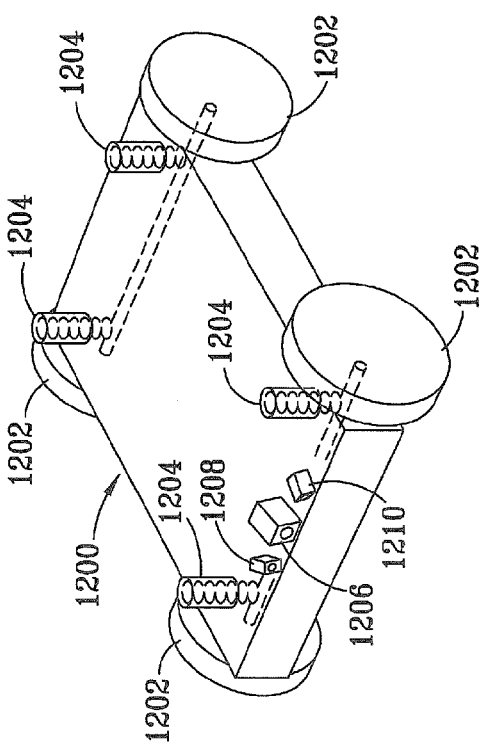
FIG. 12 exemplifies a crawler embodying features of the present invention for supporting the ACFM unit.

Accordingly, FIG. 12 exemplifies a crawler 1200 configured for supporting the ACFM 202 according to principles of an alternative embodiment of the present invention. The crawler 1200 preferably includes at least three wheels, preferably four wheels, 1202 which are preferably magnetized to adhere to the inside surface 206 of vessel 12 (FIG. 14) and allow viewing of surface welds close-up at various angles. Wheels 1202 are preferably provided with spring suspensions 1204 to facilitate travel over rough-surface welds and weld overlays on the interior surface. As discussed in further detail below, in addition to ACFM unit 202, crawler 1200 also includes lights, lasers, and cameras.

Figure 13:
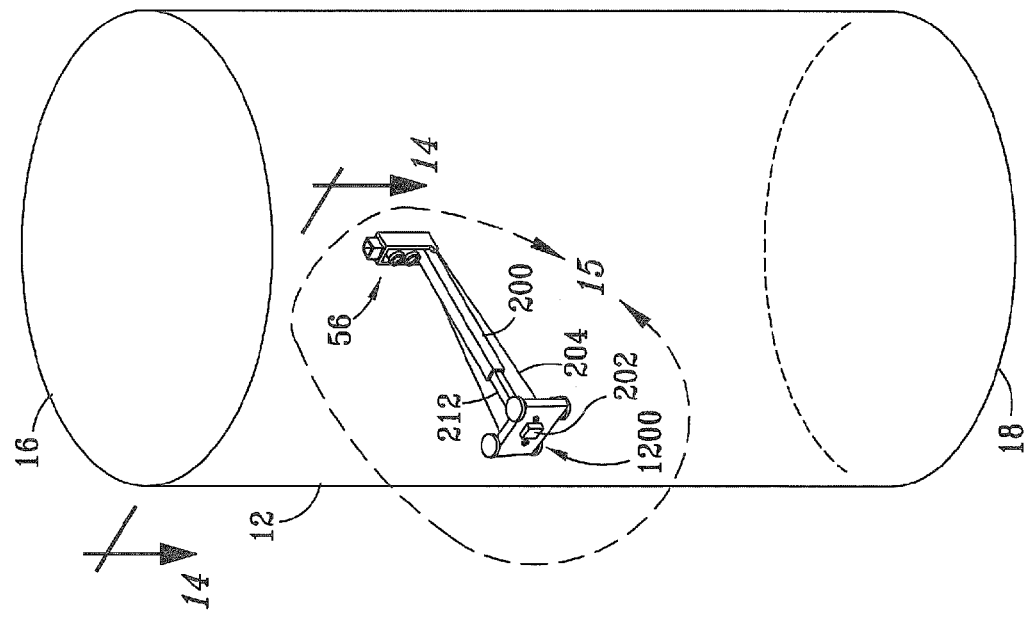
FIG. 13 is a perspective view exemplifying the crawler of FIG. 12 positioned on an interior wall of a vessel to be inspected.
Figure 14:
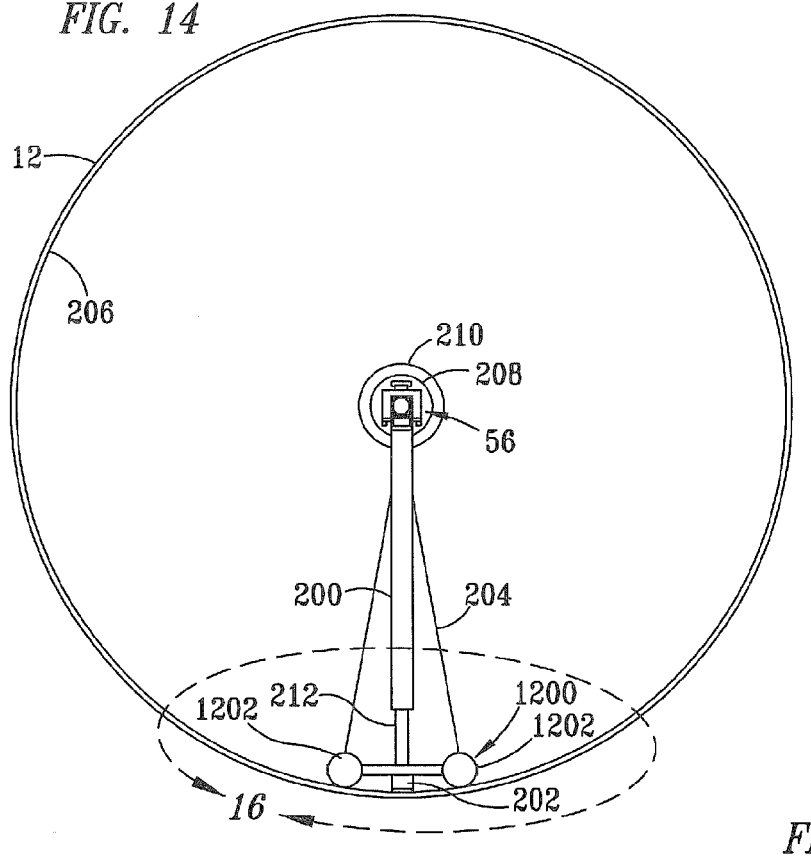
FIG. 14 is a top view of the crawler of FIG. 13.
Figure 15:
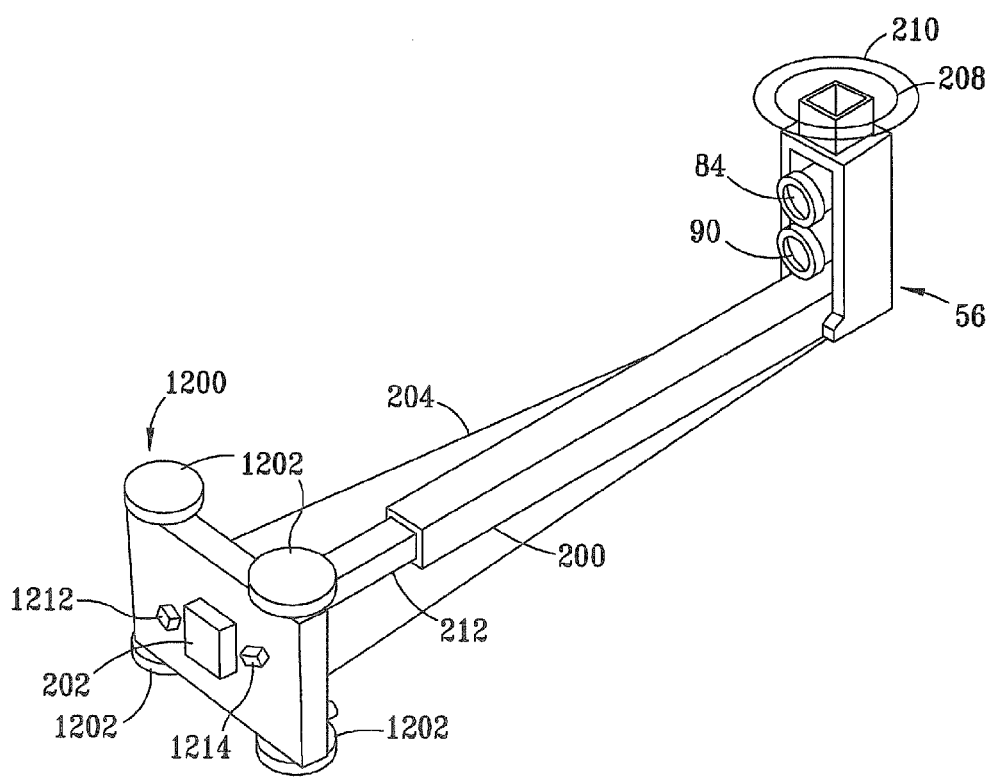
FIG. 15 is a perspective view of the crawler taken within dashed outline 15 of FIG. 13.

FIG. 13 exemplifies the crawler of FIG. 12 positioned on an interior wall of a vessel to be inspected, and FIG. 14 shows a top view of the crawler of FIG. 13. FIG. 15 is a perspective view of the crawler taken within dashed outline 15 of FIG. 13.

Figure 16:
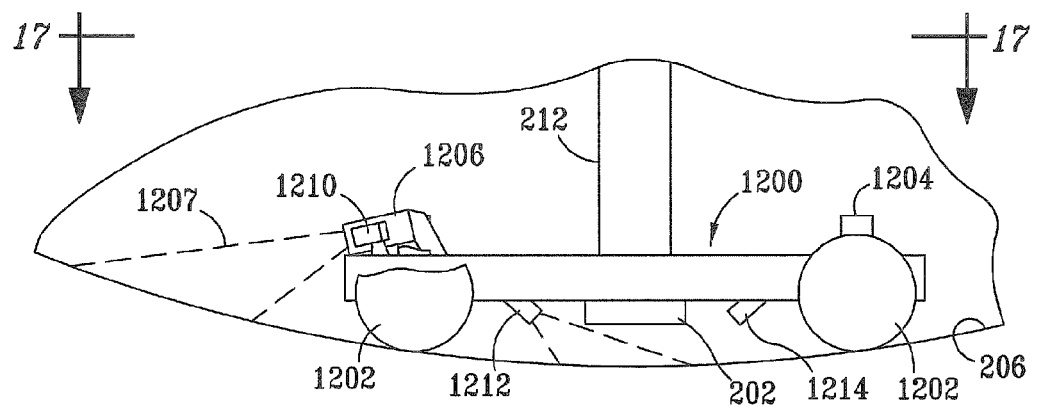
FIG. 16 is a view of the crawler of FIG. 12 taken within dashed outline 16 of FIG. 14.
Figure 17:
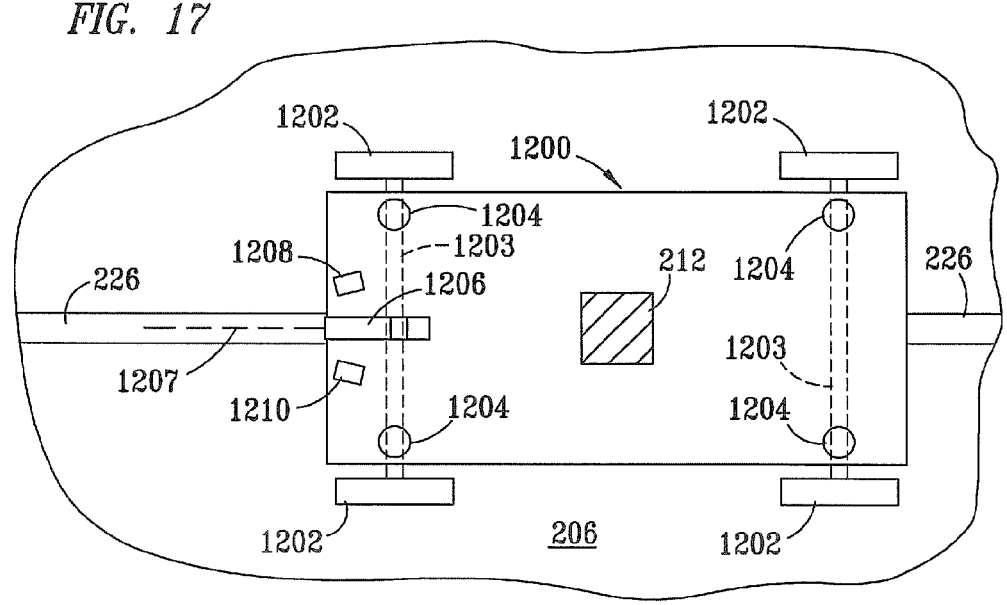
FIG. 17 is a view of the crawler of FIG. 12 taken along the line 17-17 of FIG. 16.

FIG. 16 depicts the crawler of FIG. 12 taken within dashed outline 16 of FIG. 15, and FIG. 17 is a view of the crawler of FIG. 12 taken along the line 17-17 of FIG. 16. As shown therein, the ACFM 202 is positioned on the underside of the crawler, and is preferably centered thereunder. A camera 1214 and light 1212 are also preferably positioned on the underside of the crawler, proximate to ACFM 202 for viewing welds 226 being tested by the ACFM.

A laser 1206 is positioned on a frontal portion of the crawler 1200 and is configured for projecting a line via a sheet of laser light 1207 for alignment with a weld 226 on the surface 206 of the vessel 12 to thereby facilitate remote steering by an operator. The sheet of laser light 1207 is oriented perpendicularly to the travel surface 206 of the vessel wall which then intersects the wall on a line, thereby casting a line, preferably on a weld bead, ahead of the centerline of the crawler. A camera 1208 and light 1210 are also mounted on the frontal portion of the crawler 1200 and are oriented for viewing the sheet of laser light 1207 preferably aligned with a weld 226. The cameras 1208 and 1214 are coupled via line 214 to communication imagery data to device 216 and then via line 218 to PC controller 220. It can be appreciated that the combination of laser 1206, camera 1208, and light 1210 enable an operator to guide the crawler 1200 precisely along a weld, resulting in more reliable testing by the ACFM.

Figure 18:
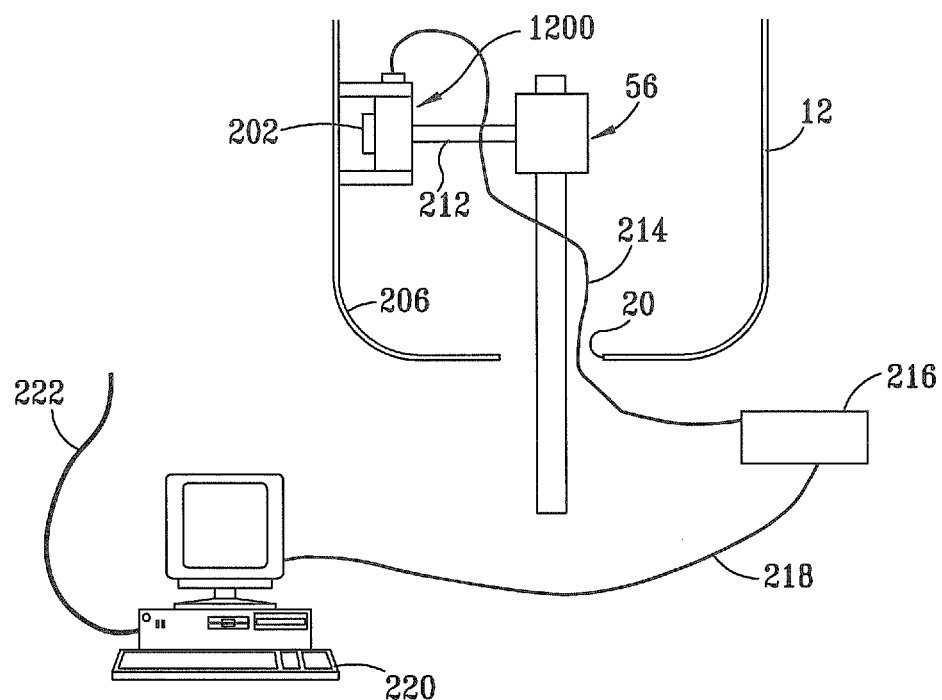
FIG. 18 is a schematic diagram of the system, incorporating the crawler of FIG. 12, for detecting and determining the severity of cracks.
Figure 19:
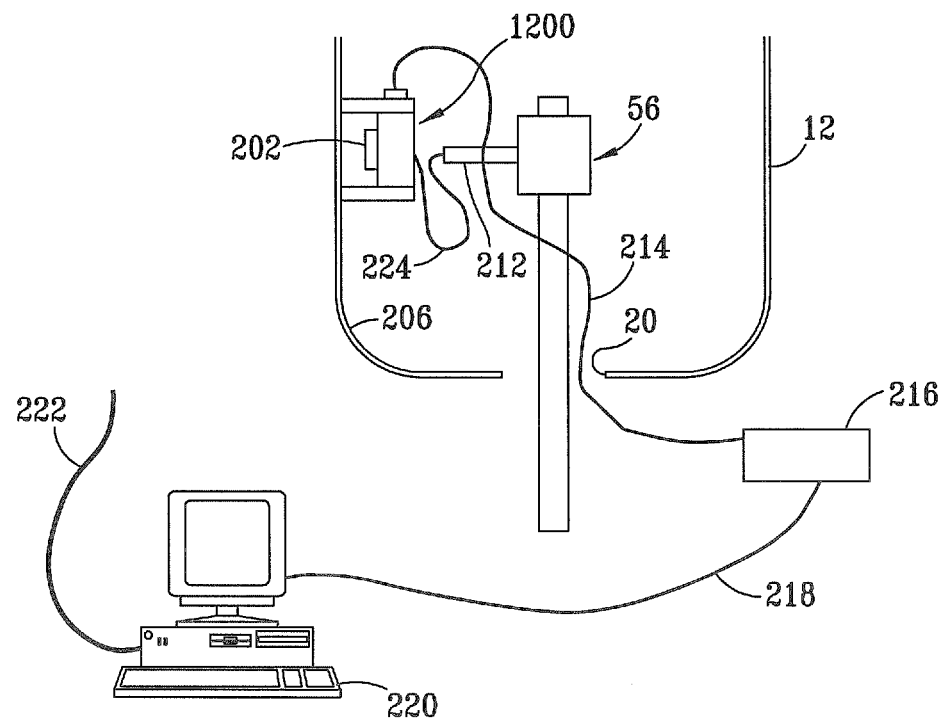
FIG. 19 is a schematic diagram of the system of FIG. 18 with the ACFM unit connected to the arm by a tether.

FIG. 18 is a schematic diagram of the system, incorporating the crawler of FIG. 12, for detecting and determining the severity of cracks, and FIG. 19 is a schematic diagram of the system of FIG. 18 with the ACFM unit connected to the arm by a tether. In addition to positioning data and test data, imagery captured by the cameras 1208 and 1214 is also passed via line 214 to communication device 216 and then via line 218 to PC controller 220.

Operation of the system depicted by FIGS. 12-19 is similar to operation of the system of FIGS. 1-11, but for additional data provided by the combination of laser 1206, lights 1210 and 1212, and cameras 1208 and 1214, which enable an operator to more precisely guide the crawler and test the weld via ACFM 202, and visually observe close-up the inside of the inspected vessel.

By the use of the system of the present invention, not only can large bulges and the like be detected using the laser system and visible defects detected by the use of the camera, but invisible defects which may be covered with residual material on the inside of a vessel can be detected using the ACFM system. The ACFM units are well known to those skilled in the art for the determination of such defects in metal surfaces.

According to the present invention, superior results are accomplished since visible defects, invisible small defects, such as corrosion pits, stress cracks and pits are readily detected as well as larger bulges and changes in the inside dimensions of the vessel. This is a very desirable result and is achieved by the use of a synergistic combination of the three measuring techniques used. The present invention is particularly well suited for use with delayed petroleum coking drums, sometimes referred to as delayed petroleum coking vessels. These vessels have openings at both the top and the bottom, which are typically co-axially positioned relative to the vertical axis of the coking drum which is sometimes referred to as a delayed petroleum coking vessel. The vessels also have a stem used to cut petroleum coke from the drum, but which can also be used to position the frame. The coke is removed with a high-pressure water jet which may leave some areas, especially where cracks or other defects may be positioned, less completely cleaned of coke. Testing of these defects is necessary to insure safe operation of the coking drum. Thus such vessels are well adapted to the use of the present invention and require testing which has not previously been available without more expensive and time consuming processes.

While the invention has been discussed by reference to the drill stem of a petroleum coking drum as a support for the frame, it should be understood that any suitable support capable of holding a frame at a selected axial location and a selected rotational and longitudinal position relative to an axis may be used. Desirably the frame is moveable longitudinally and rotationally relative to the inside of the vessel.

While the present invention has been described by reference to certain of its preferred embodiments, it is pointed out that the embodiments described are illustrative rather than limiting in nature and that many variations and modifications are possible within the scope of the present invention. Many such variations and modifications may be considered obvious and desirable by those skilled in the art based upon a review of the foregoing description of preferred embodiments.

The invention claimed is:

1. A vessel inspection system for inspecting the interior surface of a delayed petroleum coking vessel to determine defects and dimensional changes in the vessel, the system including a device comprising:
   a) frame;
   b) a support for supporting the frame for movement within the vessel along a vertical axis;
   c) a rotary positioner adapted to position the frame rotationally with respect to a vertical axis;
   d) an enclosure for electronics and a source of pressurized gas connected to the enclosure to pressurize the enclosure to minimize incursion of combustible vapor into the enclosure;
   e) a video camera supported on the frame and operably connected to at least one of a monitor and a recording means for providing video scanning of the interior surface of the vessel;
   f) a camera positioner supported on the frame and operable to position the video camera for viewing by the video camera, the camera positioner being operable to position the video camera about a second axis perpendicular to the rotary positioner;
   g) a floodlight supported on the frame for illuminating the interior surface of the vessel for viewing by the video camera;
   h) a support on the vessel for clamping the support in a predetermined lateral and vertical position with respect to the vertical axis of the vessel during operation of the system;
   i) a crawler positioned on an arm extension from at least one of the support and the frame for positioning the crawler proximate to all or selected portions of the interior of the vessel to be tested;
   j) an Alternating Current Field Measurement (ACFM) unit mounted on the crawler for testing the all or selected portions of the interior of the vessel;
   k) a crawler positioner for positioning the crawler and ACFM unit in selected locations; and
   l) a recorder coupled to the ACFM unit for recording signals indicative of the ACFM unit position and the ACFM unit data from the selected locations.

2. The system of claim 1 wherein the crawler includes a laser for generating a sheet of laser light along a weld for aligning the ACFM to the weld.

3. The system of claim 1 wherein the crawler includes a camera and a light positioned on a frontal portion of the crawler for viewing a weld line in front of the crawler.

4. The system of claim 1 wherein the crawler includes a camera and a light positioned on an underside of the crawler for viewing a weld line proximate to the ACFM.

5. The system of claim 1 wherein the crawler includes at least three wheels for facilitating movement along the interior of the vessel.

6. The system of claim 1 wherein the crawler includes at least three magnetic wheels for facilitating movement along the interior of the vessel with magnetic adherence to the interior of the vessel.

7. The system of claim 1 wherein the crawler includes at least three wheels for facilitating movement along the interior of the vessel, at least one of which wheels is mounted with spring suspension.

8. The system of claim 1 wherein the support is adapted to support the frame for movement along the vertical axis of the vessel and support the frame at a selected vertical position relative to the vertical axis.

9. The system of claim 1 wherein a pressurized gas source is positioned in fluid communication with the frame to inject a gas stream into the frame at a pressure greater than the pressure in the vessel.

10. The system of claim 1 wherein a pressurized gas source is positioned in fluid communication with the frame to inject a gas stream into the ACFM unit at a pressure greater than the pressure in the vessel.

11. The system of claim 1 wherein the ACFM unit includes magnetic wheels to support the ACFM unit at a selected spacing from the interior surface of the vessel.

12. The system of claim 1 wherein the ACFM unit is self-propelled.

13. The system of claim 1 wherein the ACFM unit is moved relative to the interior surface of the vessel by the arm extension.

14. The system of claim 1 wherein the arm extension is extendible and retractable.

15. The system of claim 1 wherein the extendible arm is rotatable relative to the vertical axis.

* * * * *